United States Patent
El-Nachef

(10) Patent No.: US 12,226,489 B2
(45) Date of Patent: Feb. 18, 2025

(54) COMPOUNDS AND METHODS FOR TREATING GASTROINTESTINAL DISEASE

(71) Applicant: The Regents of the University of California, Oakland, CA (US)

(72) Inventor: Wael N. El-Nachef, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 953 days.

(21) Appl. No.: 17/279,864

(22) PCT Filed: Sep. 26, 2019

(86) PCT No.: PCT/US2019/053064
§ 371 (c)(1),
(2) Date: Mar. 25, 2021

(87) PCT Pub. No.: WO2020/069065
PCT Pub. Date: Apr. 2, 2020

(65) Prior Publication Data
US 2022/0031854 A1    Feb. 3, 2022

Related U.S. Application Data

(60) Provisional application No. 62/738,162, filed on Sep. 28, 2018.

(51) Int. Cl.
*A61K 47/54*    (2017.01)
*A61K 47/55*    (2017.01)

(52) U.S. Cl.
CPC ............ *A61K 47/554* (2017.08); *A61K 47/55* (2017.08)

(58) Field of Classification Search
CPC .............................. A61K 47/554; A61K 47/55
USPC ......................................................... 514/171
See application file for complete search history.

(56) References Cited

U.S. PATENT DOCUMENTS

2011/0195935 A1    8/2011    Farber

FOREIGN PATENT DOCUMENTS

| EP | 3348548 A1 | 7/2018 |
|---|---|---|
| WO | WO-2004/012686 A2 | 2/2004 |
| WO | WO-2006/102071 A1 | 9/2006 |
| WO | WO-2011/160974 A2 | 12/2011 |
| WO | WO-2017/041701 A1 | 3/2017 |
| WO | WO-2020/069065 A1 | 4/2020 |

OTHER PUBLICATIONS

Abdellatif et al., "Dinitroglyceryl and diazen-1-ium-1,2-diolated nitric oxide donor ester prodrugs of aspirin, indomethacin and ibuprofen: synthesis, biological evaluation and nitric oxide release studies," Bioorg Med Chem Letts 19(11):3014-3018 (2009).
Batta et al., "Synthesis and intestinal metabolism of ursodeoxycholic acid conjugate with an antiinflammatory agent, 5-aminosalicylic acid," J Lipid Res 39(8):1641-1646 (1998).
Caira et al., "Drug Metabolism: Current Concepts," (2006).
Carini et al., "In vitro metabolism of a nitroderivative of acetylsalicylic acid (NCX4016) by rat liver: LC and LC-MS studies," J Pharma Biomed Anal 29(6):1061-1071 (2002).
Gao et al., "In vitro metabolism of nitric oxide-donating aspirin: the effect of positional isomerism," J Pharma Exp Ther 312(3):989-997 (2005).
Govoni et al., "In vitro metabolism of (nitrooxy)butyl ester nitric oxide-releasing compounds: comparison with glyceryl trinitrate," J Pharma Exp Ther 317(2):752-761 (2006).
Govoni et al., "Metabolism and pathways for denitration of organic nitrates in the human liver," J Pharma Exp Ther 346(1):96-104 (2013).
International Search Report and Written Opinion for International Application No. PCT/US2019/053064 dated Nov. 26, 2019.
Lazzarato et al., "Searching for new NO-donor aspirin-like molecules: a new class of nitrooxy-acyl derivatives of salicylic acid," J Med Chem 51(6):1894-1903 (2008).
Rolando et al., "Synthesis physicochemical profile and PAMPA study of new NO-donor edaravone co-drugs," Bioorg Med Chem 20(2):841-850 (2012).
Turnbull et al., "Therapeutic effects of nitric oxide-aspirin hybrid drugs," Exp Opin Ther Targs, 10(6):911-922 (2006).
Lotfy et al., "Recent progress in the use of glucagon and glucagon receptor antagonists in the treatment of diabetes mellitus." The Open Medicinal Chemistry Journal 8 (2014): 28-35.
Yi, "Design, Synthesis and Bioactivity of NO donor DPP-4 Inhibitors" China's Excellent Master's Thesis Full Text Database Engineering Science and Technology Series I, Issue 04, No. Page 1-63 (2015).

*Primary Examiner* — Kristin A Vajda
(74) *Attorney, Agent, or Firm* — Foley Hoag LLP; David P. Halstead

(57) ABSTRACT

The present disclosure relates to chemical moieties which, when bonded to pharmacophores, cause the pharmacophores to undergo first pass metabolism. By undergoing first pass metabolism, a pharmacophore may be made less bioavailable. Such compounds and related pharmaceutical compositions may be used for targeted treatment of diabetic and non-diabetic gastrointestinal disorders, with minimal systemic circulation beyond the gastrointestinal tract.

12 Claims, No Drawings

COMPOUNDS AND METHODS FOR TREATING GASTROINTESTINAL DISEASE

RELATED APPLICATIONS

This application is a U.S. National Stage Application of International Application No. PCT/US19/53064, filed Sep. 26, 2019; which claims the benefit of priority to U.S. Provisional Patent Application No. 62/738,162, filed Sep. 28, 2018, both of which are hereby incorporated by reference in their entireties.

BACKGROUND

Type 2 diabetes mellitus (DM2) is estimated to affect up to 12% of all persons living in the US.[1] Unfortunately, the incidence of DM2 is increasing, particularly in the pediatric population.[2] The metabolic and vascular sequelae of DM2 are well known; however, patients with DM2 also suffer from enteric neuropathies that can involve the stomach (gastroparesis), the small bowel (small intestinal bacterial overgrowth [SIBO]), and the colon (slow transit constipation).[3-6] These conditions can devastate quality of life and interfere with nutrition, which in turn complicates efforts to achieve euglycemia.[3-7] The prevalence of these gastrointestinal conditions is not well established, but studies estimate that up to 20% of diabetic patients have altered gastric motility,[8] and the rate of hospitalization for diabetic gastroparesis increased 158% between 1995 and 2004.[9] Some of the current medical therapy available in the US for gastroparesis carries the risk of permanent neurologic complications (tardive dyskinesia),[10-12] while treatment for SIBO is costly and not durable,[6,13] with the majority of patients expected to relapse.

Accordingly, there exists a need to develop further compositions for treating diabetic and non-diabetic gastrointestinal diseases.

SUMMARY OF INVENTION

The present disclosure relates to creating a medicinal compartment in the body comprised of the luminal gastrointestinal tract wherein a medication achieves a therapeutically effective amount (the concentration of a compound that is sufficient to elicit the desired therapeutic effect) while having a low concentration in systemic circulation (e.g., below 50% of an effective concentration, or even below 10% of an effective concentration). In certain embodiments, the present disclosure relates to compounds comprising a pharmacophore and a targeting moiety, wherein the targeting moiety causes the pharmacophore to undergo first pass metabolism, preferably to a significant extent, e.g., such that the plasma level of the compound remains below an effective concentration, preferably below 50% of an effective concentration, or even below 10% of an effective concentration.

The present disclosure further relates to pharmaceutical compositions comprising such compounds, as well as methods of administering such compounds, e.g., by administering the compound to a subject suffering from diabetic or non-diabetic gastrointestinal disorders.

The present disclosure further relates to methods for treatment of diabetic or non-diabetic gastrointestinal disorders in a subject in need thereof, comprising administering such compounds.

In other embodiments, the present disclosure relates to a chemical moiety, wherein when the moiety is covalently bonded to a pharmacophore, the moiety causes the pharmacophore to undergo first pass metabolism, preferably to a significant extent, e.g., such that the plasma level of the compound remains below an effective concentration, preferably below 50% of an effective concentration, or even below 10% of an effective concentration.

DETAILED DESCRIPTION OF THE INVENTION

In certain embodiments, the compounds of the present disclosure may be used to treat certain complications of DM2, such as by treating the underlying pathophysiology specific to those complications of DM2. Complications of DM2 that may be treated with compounds of the present disclosure include, but are not limited to, gastroparesis, SIBO, and constipation. The compounds may be used to treat diabetic patients, including, but not limited to, diabetic patients with symptoms of gastroparesis, symptoms of SIBO, and/or symptoms of constipation, or to treat non-diabetic patients with similar conditions. The compounds are designed to act within the gastrointestinal tract and to be quickly processed in the liver and eliminated from the patient's portal circulation before reaching the systemic circulation, thereby reducing or eliminating systemic side effects. The compounds of the present disclosure may be orally administered one or more times daily, such as immediately prior to each meal, with a meal, or after a meal. Furthermore, the compounds may be formulated such that the active ingredient is selectively released in a target component of the gastrointestinal tract (e.g. stomach vs. small intestine vs. colon), depending on the patient's condition and/or symptoms.

In certain embodiments, the present disclosure is directed to a compound comprising a pharmacophore and a targeting moiety; wherein the targeting moiety causes the pharmacophore to undergo significant first pass metabolism, e.g., in the liver.

By undergoing significant first pass metabolism, the pharmacophore may be made less systemically bioavailable, for example, to selectively expose the gastrointestinal tract to the pharmacophore, with limited exposure into the systemic circulation. Systemic bioavailability is a key pharmacokinetic parameter expressing the proportion of a drug administered by a nonvascular route that gains access to the systemic circulation. As used herein, the term "systemic bioavailability" is art-recognized and refers to the extent and the rate at which a substance or its active moiety is delivered from a pharmaceutical form and becomes available in the systemic circulation.[14] Systemic bioavailability may be measured using any suitable means known in the art, including, but not limited to, those used to measure pharmacokinetic parameters such as AUC, $C_{max}$, and $T_{max}$.

In various embodiments, the systemic bioavailability is less than 10%, less than 5%, or even less than 1%. As used herein, systemic bioavailability expressed as a percent refers to the percentage of the molar mass ingested. Systemic bioavailability (%) can be measured using any suitable means known in the art. For example, systemic bioavailability can be assessed by sampling the portal vein (pre-hepatic) and superior vena cava/right atrium (post-hepatic). Additionally, depending on the compound, protease inhibitors can be added to freshly collected blood to prevent degradation. For example, peptides can be protected from degradation by adding basic trypsin inhibitor of bovine pancreas (also known as "aprotinin").

In certain embodiments, the targeting moiety comprises at least one nitrate ester (—ONO$_2$) group, preferably at least two nitrate ester groups. In certain such embodiments, the targeting moiety is selected from:

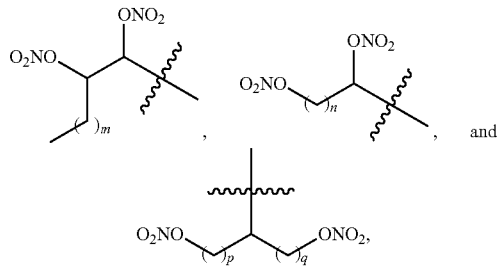

wherein n, p, and q are each independently integers from 1-4; and
m is an integer from 0-5.

For example, the targeting moiety may be

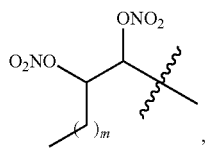

e.g., wherein m is an integer from 1-5.

Alternatively, the targeting moiety may be

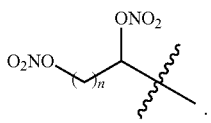

In certain such embodiments, n is 1. In other such embodiments, n is an integer from 2-4.

Similarly, the targeting moiety may be

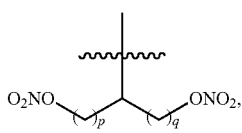

e.g., wherein p and q are each 1.

In still further embodiments, the targeting moiety comprises at least three nitrate ester groups.

For example, the targeting moiety may be

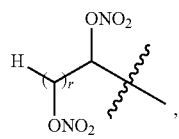

wherein r is an integer from 1-6, e.g., from 2-6.

In certain preferred embodiments, the targeting moiety comprises a residue of a bile acid, e.g., ursodeoxycholic acid. Without wishing to be bound to any particular theory, it is believed that using a bile acid has the added advantage of promoting enterohepatic circulation, and thus may increase bioavailability within the gastrointestinal lumen compartment.

The pharmacophore and the targeting moiety may be directly linked or linked through a linking moiety, such as an alkyl chain and/or one or more functional groups comprising bonds that are not readily cleaved under physiological conditions, such as amides, ureas, carbamates, ethers, amines, sulfones, and heterocycles (e.g., heterocycles formed by click chemistry, such as [3+2] cycloadditions of alkynes with nitrile oxides, azides, and the like).

Suitable pharmacophores include chemical moieties capable of interacting with (e.g., activating or inactivating, agonizing or antagonizing) a biological receptor, preferably on a selective basis. In some embodiments, a pharmacophore is essentially a drug molecule that is covalently attached to the rest of the compound; that is, a pharmacophore, when attached to the aforementioned moieties, retains its ability to interact with the receptor that it targets as part of the compound and has biological activity of its own.

In certain embodiments, the pharmacophore is a residue of an anti-diabetes agent, such as a dipeptidyl peptidase-4 inhibitor, a glucagon-like peptide-1 agonist, a glucagon receptor antagonist, or a glucagon-like peptide-2 agonist; additional pharmacophores can be residues of a pro-motility agent, an immune modulator, an inflammation modulating drug, or an anti-neoplastic agent. In certain embodiments, the anti-diabetes agent is a glucagon receptor antagonist, such as isoserine, beta-alanine derivatives, bicyclic 19-residue peptide BI-32169, Des-His1-[Glu9] glucagon amide, 5-hydroxyalkyl-4-phenylpyridine, N-[3-cano-6-(1,1 dimethylpropyl)-4,5,6,7-tetrahydro-1-benzothien-2-yl]-2-ethylbutamide, Skyrin and NNC 250926. Isoserine has the following structure:

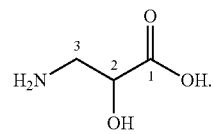

In some aspects, the glucagon receptor antagonist is NNC 250926. NNC 250926 has the following structure:

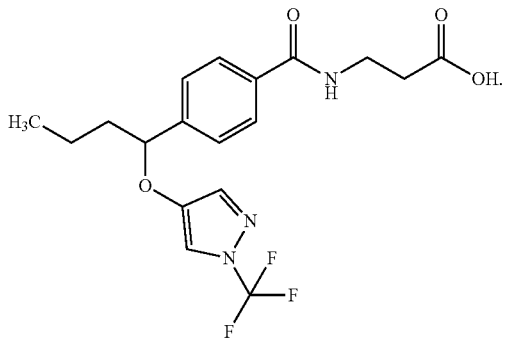 [SMILES: CCCC(Oc1cnn(C(F)(F)F)c1)c1ccc(C(=O)NCCC(=O)O)cc1]

Examples of compounds according to the present disclosure wherein the pharmacophore is NNC 250926 include, but are not limited to, the following:

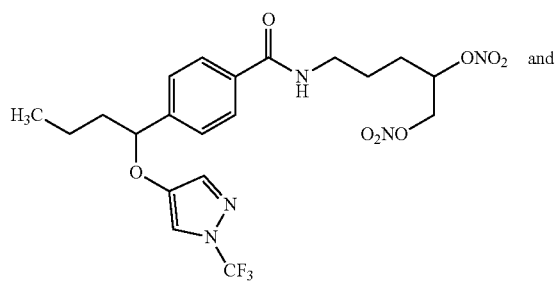

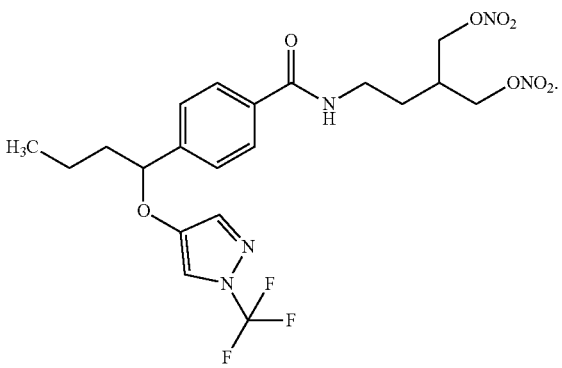

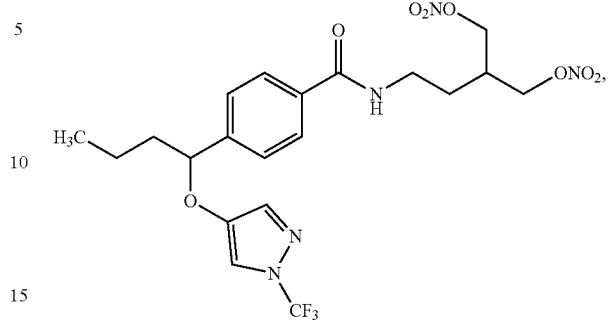

For example, the compound may have the structure:

or a pharmaceutically acceptable salt thereof.

Similarly, the compound may have the structure:

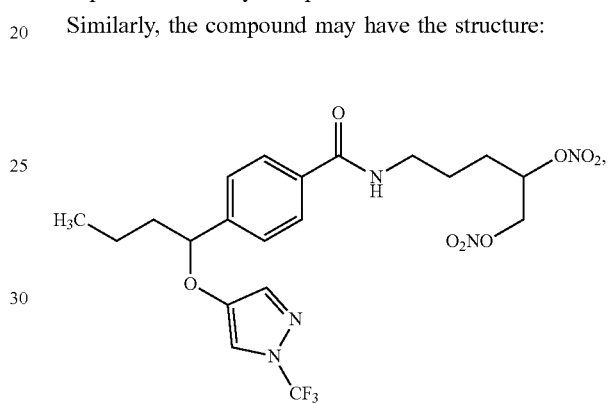

or a pharmaceutically acceptable salt thereof.

A person of ordinary skill in the art would appreciate that a bioactive drug compound can be incorporated as a pharmacophore into the compounds of the invention in any one of a variety of spatial orientations, and at any one of a variety of substitutable positions, as described herein. A person of ordinary skill in the art can readily synthesize a number of such compounds in order to determine which orientations and connectivities exhibit acceptable biological activity for a given application. In example embodiments, a compound with a pharmacophore having appropriate orientation and connectivity retains the type of biological activity of the parent bioactive drug compound, though the activity of the compound bearing the pharmacophore may be stronger or weaker than that of the parent bioactive drug compound. In certain embodiments, a suitable orientation and connectivity is determined when the pharmacophore exhibits at least 99%, 98%, 95%, 90%, 85%, 80%, 75% 70%, 65%, 60%, 55%, or 50% of the biological activity of parent compound.

Typically, the compounds of the present disclosure are configured to be substantially susceptible to first pass metabolism in the liver, e.g., such that the pharmacophore has low systemic bioavailability. For example, bonds that link the pharmacophores to the scaffold of the targeting moiety are preferably not hydrolyzed under physiologic conditions (e.g., lack ester, thioester, acetal, ketal, or other acid- or base-labile bonds).

In certain embodiments, the pharmacophore is selected to limit transition from the portal circulation to the systemic circulation, e.g., to limit absorption through the gut. While molecular size is one factor that can contribute to a molecule's resistance to transition into the systemic circulation from the portal circulation, charge and polarity can play an important role as well.

In certain embodiments, the present disclosure is directed to a chemical moiety, wherein, when the moiety is covalently bonded to a pharmacophore, the moiety causes the pharmacophore to undergo first pass metabolism. In certain such embodiments, the chemical moiety inhibits the pharmacophore from undergoing first pass metabolism in the pre-hepatic gut and/or causes the pharmacophore to undergo first pass metabolism in the liver. In certain embodiments, the chemical moiety comprises at least one nitrate ester (—ONO$_2$) group, preferably at least two nitrate ester (—ONO$_2$) groups. In certain such embodiments, the chemical moiety is selected from:

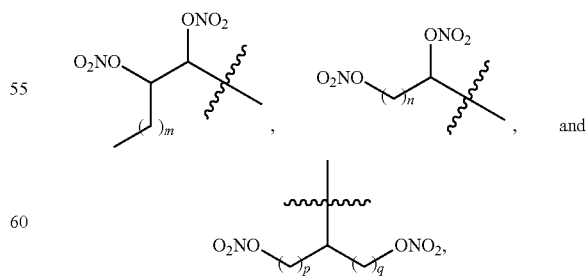

wherein n, p, and q are each independently integers from 1-4; and m is an integer from 0-5.

For example, the chemical moiety may be

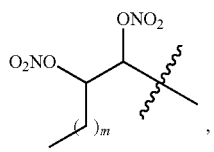

e.g., wherein m is an integer from 1-5.

Alternatively, the chemical moiety may be

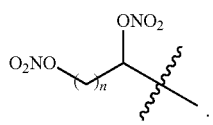

In certain such embodiments, n is 1. In other such embodiments, n is an integer from 2-4.

Similarly, the chemical moiety may be

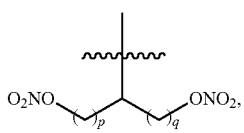

e.g., wherein p and q are each 1.

In still further embodiments, the chemical moiety comprises at least three nitrate ester (—ONO$_2$) groups.

For example, the chemical moiety may be

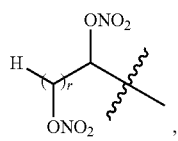

wherein r is an integer from 1-6, e.g., an integer from 2-6.

In preferred embodiments, the chemical moiety comprises a residue of a bile acid, such as ursodeoxycholic acid, which has the added advantage of favoring enterohepatic circulation and thus may increase bioavailability within the gastrointestinal lumen compartment.

In yet another aspect, the present disclosure is related to a method of inducing first pass metabolism of a pharmacophore, comprising covalently attaching the chemical moiety to a pharmacophore.

In another aspect, the invention provides pharmaceutical compositions comprising the compounds described herein, optionally in admixture with one or more pharmaceutically acceptable excipients. Preferably, the compositions are suitable for oral administration, whether as solids (tablets, capsules, caplets, etc.), liquids (suspensions, solutions, etc.), or other orally administered formulations.

In yet another aspect, the invention provides methods for administering the compounds described herein, e.g., by administering an effective amount of the compound to a subject suffering from diabetic or non-diabetic gastrointestinal disorders, preferably diabetes.

Similarly, the present disclosure provides methods for treating diabetic or non-diabetic gastrointestinal disorder in a subject in need thereof, comprising administering to the subject a compound described herein. In certain preferred embodiments, the method is a method for treating diabetes.

In certain embodiments, compounds of the invention may have one or more chiral centers, whether in the pharmacophore, the targeting moiety, or the linking moiety. In certain such embodiments, compounds of the invention may be enriched in one or more diastereomers or one or more enantiomers. For example, a compound of the invention may have greater than 30% de, 40% de, 50% de, 60% de, 70% de, 80% de, 90% de, or even 95% or greater de. A diastereo-enriched composition or mixture may comprise, for example, at least 60 mol percent of one diastereomer, or more preferably at least 75, 90, 95, or even 99 mol percent. In certain embodiments, the compound enriched in one diastereomer is substantially free of the other diastereomers, wherein substantially free means that the other diastereomers make up less than 10%, or less than 5%, or less than 4%, or less than 3%, or less than 2%, or less than 1% as compared to the amount of the primary diastereomer, e.g., in the composition or compound mixture. For example, if a composition or compound mixture contains 98 grams of a first diastereomer and 2 grams of a second diastereomer, it would be said to contain 98 mol percent of the first diastereomer and only 2% of the second diastereomer. In certain embodiments, a compound of the invention may have greater than 30% ee, 40% ee, 50% ee, 60% ee, 70% ee, 80% ee, 90% ee, or even 95% or greater ee. An enantio-enriched composition or mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the other enantiomer makes up less than 10%, or less than 5%, or less than 4%, or less than 3%, or less than 2%, or less than 1% as compared to the amount of the primary enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer. The compounds of the invention may also be racemic mixtures of enantiomers.

Compounds of any of the structures described herein and any composition of these compounds may be used in the manufacture of medicaments for the treatment of any diseases or conditions disclosed herein.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x\text{-}y}$" when used in conjunction with a chemical moiety, such as, acyl, acyloxy, alkyl, alkenyl, alkynyl, or alkoxy is meant to include groups that contain from x to y carbons in the chain. For example, the term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

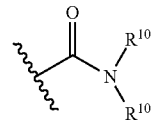

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

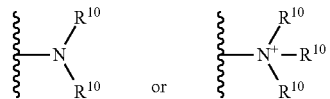

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

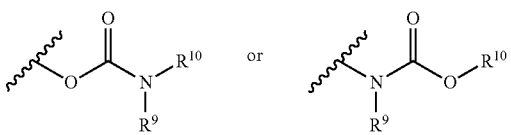

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

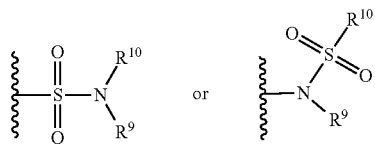

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

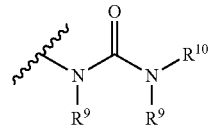

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). As used herein, treating a disease, disorder, or condition includes treating complication(s) of the disease, disorder, or condition, such as by treating the underlying pathophysiology specific to the complication(s) of the disease, disorder, or condition.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

The term "masking moiety" as used herein, refers to the chemical moiety that is a covalently bound modification of a pharmacophore that renders the compounds of the present invention to which it is attached prodrugs. A masking moiety is cleavable under, for example, acidic conditions, basic conditions, or physiologic conditions. When the masking moiety is cleaved, the prodrugs are converted to the therapeutically active agents of the present invention. Esters and carbonates can be used to mask hydroxyls, carbamates and amides can be used to mask amines, carboxyls can be masked as esters, etc., and in certain embodiments the precise masking moiety can be selected to be cleaved under conditions particular to a region of the digestive tract. For example, an amine or hydroxyl can be acylated by a 4-aminobutanoyl group, to form a prodrug that can be administered as a salt of the amine. In the acidic conditions of the stomach, the amino group will remain protonated, masking its nucleophilicity. In the more basic conditions of the small intestines, the ammonium group will be deprotonated, revealing the nucleophilic amine, which can nucleophilicly attack the amide or ester formed by the butanoyl group, ultimately revealing the amide or ester with the concomitant release of the protecting group as a lactam.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or organic esters.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules). In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively or additionally, compositions can be formulated for delivery via a catheter, stent, wire, or other intraluminal device. Delivery via such devices may be especially useful for delivery to the gastrointestinal tract.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In certain embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

REFERENCES

1. Centers for Disease Control and Prevention. National Diabetes Statistics Report, 2017. In: Centers for Disease Control and Prevention, ed. Atlanta, Ga.: U.S. Dept of Health and Human Services; 2017.
2. Mayer-Davis E J, Lawrence J M, Dabelea D, et al. Incidence Trends of Type 1 and Type 2 Diabetes among Youths, 2002-2012. *The New England journal of medicine.* 2017; 376(15):1419-1429.
3. Camilleri M. Clinical practice. Diabetic gastroparesis. *The New England journal of medicine.* 2007; 356(8):820-829.
4. Chandrasekharan B, Srinivasan S. Diabetes and the enteric nervous system. *Neurogastroenterology and motility: the official journal of the European Gastrointestinal Motility Society.* 2007; 19(12):951-960.
5. Adamska A, Nowak M, Pilacinski S, et al. Small intestinal bacterial overgrowth in adult patients with type 1 diabetes: its prevalence and relationship with metabolic control and the presence of chronic complications of the disease. *Polskie Archiwum Medycyny Wewnetrznej.* 2016; 126(9): 628-634.
6. Gotfried J, Priest S, Schey R. Diabetes and the Small Intestine. *Current treatment options in gastroenterology.* 2017; 15(4):490-507.
7. Hasler W L. Gastroparesis: pathogenesis, diagnosis and management. *Nature reviews Gastroenterology & hepatology.* 2011; 8(8):438-453.

8. Camilleri M, Malagelada J R. Abnormal intestinal motility in diabetics with the gastroparesis syndrome. *European journal of clinical investigation*. 1984; 14(6):420-427.
9. Bharucha A E. Epidemiology and natural history of gastroparesis. *Gastroenterology clinics of North America*. 2015; 44(1):9-19.
10. Rao A S, Camilleri M. Review article: metoclopramide and tardive dyskinesia. *Alimentary pharmacology & therapeutics*. 2010; 31(1):11-19.
11. Pasricha P J, Pehlivanov N, Sugumar A, Jankovic J. Drug Insight: from disturbed motility to disordered movement—a review of the clinical benefits and medicolegal risks of metoclopramide. *Nature clinical practice Gastroenterology & hepatology*. 2006; 3(3):138-148.
12. Camilleri M, Parkman H P, Shafi M A, Abell T L, Gerson L. Clinical guideline: management of gastroparesis. *The American journal of gastroenterology*. 2013; 108(1):18-37; quiz 38.
13. Adike A, DiBaise J K. Small Intestinal Bacterial Overgrowth: Nutritional Implications, Diagnosis, and Management. *Gastroenterology clinics of North America*. 2018; 47(1):193-208.
14. Toutain P L, Bousquet-Mèlou. Bioavailability and its assessment. *Journal of Veterinary Pharmacology and Theraputics*. 2004; 27:455-466.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound, comprising a pharmacophore and a targeting moiety, wherein the targeting moiety causes the pharmacophore to undergo first pass metabolism; wherein the targeting moiety is selected from:

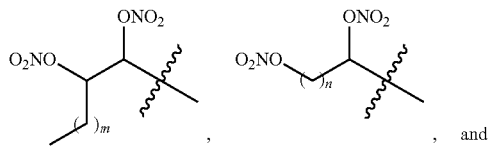
, and

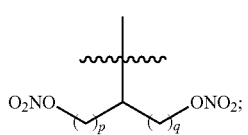

wherein n, p, and q are each independently integers from 1-4; and m is an integer from 0-5; and the pharmacophore is glucagon receptor antagonist NNC 250926 wherein NNC 250926, has the structure

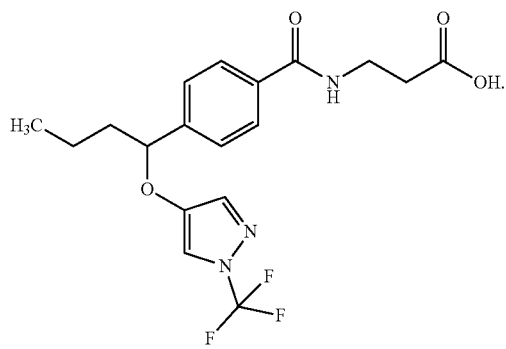 [SMILES: CCCC(Oc1cnn(C(F)(F)F)c1)c1ccc(C(=O)NCCC(=O)O)cc1]

2. The compound of claim 1, wherein the targeting moiety causes the pharmacophore to undergo first pass metabolism in the liver.

3. The compound of claim 1, wherein the systemic bioavailability is less than 1%.

4. The compound of claim 1, wherein the targeting moiety is

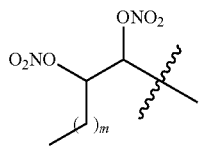

5. The compound of claim 1, wherein the targeting moiety is

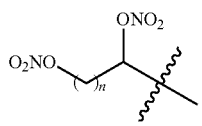

6. The compound of claim 1, wherein the targeting moiety is

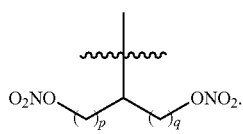

7. The compound of claim 1, wherein the pharmacophore and the targeting moiety are linked through a linking moiety.

8. The compound of claim 1, having the structure:

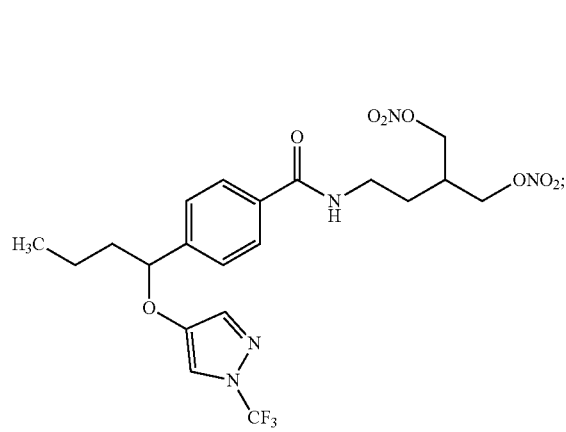

or a pharmaceutically acceptable salt thereof.

9. The compound of claim 1, having the structure:

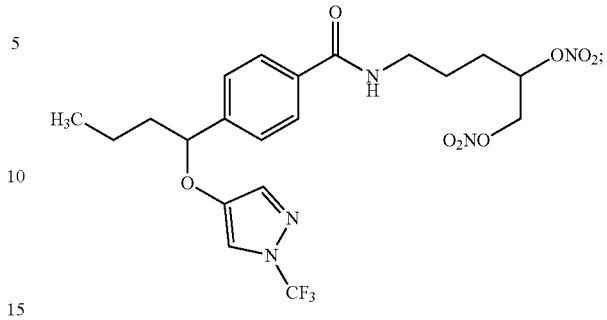

or a pharmaceutically acceptable salt thereof.

10. A pharmaceutical composition comprising a compound of claim 1, and a pharmaceutically acceptable excipient.

11. A method of administering a compound of claim 1 comprising administering an effective amount of the compound of claim 1 to a subject suffering from diabetes or a gastrointestinal disorder.

12. The method of claim 11, wherein the subject is suffering from diabetes.

* * * * *